US012633408B2

(12) United States Patent
Lo et al.

(10) Patent No.: US 12,633,408 B2
(45) Date of Patent: May 19, 2026

(54) IMAGE SCANNING POSITIONING ASSISTANCE SYSTEM

(71) Applicants:National Chengchi University, Taipei City (TW); TAICHUNG VETERANS GENERAL HOSPITAL, Taichung City (TW)

(72) Inventors: Chung-Ming Lo, Taipei City (TW); Kuo-Lung Lai, Taichung City (TW)

(73) Assignees: National Chengchi University, Taipei City (TW); TAICHUNG VETERANS GENERAL HOSPITAL, Taichung City (TW)

( * ) Notice: Subject to any disclaimer, the term of this patent is extended or adjusted under 35 U.S.C. 154(b) by 258 days.

(21) Appl. No.: 18/666,246

(22) Filed: May 16, 2024

(65) Prior Publication Data

US 2025/0104857 A1     Mar. 27, 2025

(30) Foreign Application Priority Data

Sep. 23, 2023    (TW) .................................. 112136415

(51) Int. Cl.
*G16H 40/67*        (2018.01)
*G06T 7/00*        (2017.01)
        (Continued)

(52) U.S. Cl.
CPC ........... *G16H 40/67* (2018.01); *G06T 7/0014* (2013.01); *G06V 10/761* (2022.01);
        (Continued)

(58) Field of Classification Search
CPC ...... G16H 40/67; G16H 30/20; G06V 10/761; G06V 10/764; G06T 7/0014; G06T 2207/10132
        (Continued)

(56) References Cited

U.S. PATENT DOCUMENTS

2010/0095409 A1*  4/2010  Sulzbach ............... G01Q 70/08
                                                                850/60
2015/0105098 A1*  4/2015  Sridhara ............... H04W 4/023
                                                                455/456.1
        (Continued)

*Primary Examiner* — Gabriel I Garcia
(74) *Attorney, Agent, or Firm* — RABIN & BERDO, P.C.

(57)        ABSTRACT

An image scanning positioning assistance system includes an image scanning device, an image display device, a storage device, and a processing device. The image scanning device generates a scanned image signal. The image display device displays a scanned image. The storage device stores multiple image types. The processing device calculates first classification probability values of the multiple image types corresponding to the scanned image signal, and determines whether the scanned image signal is a standard image. When the scanned image signal is the standard image, the processing device generates a standard image notification signal, and the positioning assistance notifying device generates a standard image notification. Otherwise, the processing device generates a non-standard image notification signal, and the positioning assistance notifying device generates a non-standard image notification. Therefore, the positioning assistance notifying device can notify an operator of the image scanning device for determining whether the operator is scanning accurately.

10 Claims, 9 Drawing Sheets

(51) Int. Cl.
  *G06V 10/74*  (2022.01)
  *G06V 10/764*  (2022.01)
  *G16H 30/20*  (2018.01)

(52) U.S. Cl.
  CPC ........... *G06V 10/764* (2022.01); *G16H 30/20*
      (2018.01); *G06T 2207/10132* (2013.01)

(58) Field of Classification Search
  USPC ........................................................ 382/128
  See application file for complete search history.

(56) References Cited

U.S. PATENT DOCUMENTS

| | | | |
|---|---|---|---|
| 2022/0299651 A1* | 9/2022 | Miyamoto | G01S 19/40 |
| 2023/0081403 A1* | 3/2023 | Pelissier | G06F 3/016 |
| | | | 345/177 |
| 2024/0100302 A1* | 3/2024 | Dikeman | A61B 8/488 |
| 2024/0164759 A1* | 5/2024 | Cheng | G16H 40/67 |

* cited by examiner 0.32
S_lat_med_110.jpg 0.32
S_infra_p_10375.jpg 0.30
S_infra_p_10283.jpg 0.30
S_infra_p_20366-2.jpg 0.30
S_LFTJ_20705.jpg 0.29
S_lat_med_20076.jpg 0.27
S_post_20.jpg 0.27
S_lat_med_20139.jpg 0.27
S_infra_p_10463.jpg 0.26
S_infra_p_20548.jpg

IMAGE SCANNING POSITIONING ASSISTANCE SYSTEM

CROSS-REFERENCES TO RELATED APPLICATION(S)

This application claims the priority benefit of TW application No. 112136415 filed on Sep. 23, 2023, the entirety of which is hereby incorporated by reference herein and made a part of the specification.

BACKGROUND OF THE INVENTION

1. Field of the Invention

The present invention relates to an assistance system, and especially an image scanning positioning assistance system.

2. Description of the Related Art

Under societal aging, more and more elderly people need care. Studies have stated that the elderly population will account for more than 20% in 2026, officially a "super-aged society". Therefore, the next ten years will be the "golden decade" of the age-tech. In particular, the annual long-term care budget in 2023 has exceeded 60 billion NTD in Taiwan, and the universal healthcare system has more than 800 billion NTD in related expenditures each year.

In addition, the elder people are often in poor physical conditions and need long-term tracking and monitoring. As the elder people are often restricted in mobility, doctors or nursing staff will go to communities or remote areas for medical services. In recent years, in response to the epidemic, relatively mature telemedicine services have been developed. Targets of telemedicine services will switch from geo-based focus on residents in rural areas and outlying islands to need-based focus on patients, broadening the applicable targets. The applicable targets are broadened from five categories of acute inpatients, residents of long-term care institutions, family physician plans, home medical plans, and international medical patients to further include social welfare institutions, hospices, patients with stable chronic diseases, hospice care, and patients during epidemic outbreaks.

Since the telemedicine usually requires personnel to reach the scene away from the hospital, the personnel usually carry with them some portable equipment for inspection, for example, a portable ultrasound machine or a handheld ophthalmoscope to check the physical conditions of the patients. However, the equipment requires experienced personnel for operation. If operated by personnel unfamiliar with it, the equipment may perform inaccurate checking, and it is challenging to find helping hands on the spot. Therefore, this situation needs to be improved.

SUMMARY OF THE INVENTION

The present invention provides an image scanning positioning assistance system, which can actively notify operators of a current checking status, thereby avoiding inaccurate inspection due to personnel unfamiliar with the facilities operating the image scanner.

The image scanning positioning assistance system includes an image scanning device, an image display device, a storage device, a processing device, and a positioning assistance notifying device.

The image scanning device scans a scanning area of a human body, and generates a scanned image signal.

The image display device is electrically connected to the image scanning device, receives the scanned image signal, and displays a scanned image according to the image signal.

The storage device stores a plurality of image types.

The processing device is communicatively connected to the image scanning device and the storage device, receives the scanned image signal generated by the image scanning device, and respectively calculates a plurality of first classification probability values of the multiple image types corresponding to the scanned image signal. The processing device further determines whether the scanned image signal is a standard image according to the first classification probability values.

When the scanned image signal is the standard image, the processing device generates a standard image notification signal, and stores the scanned image signal into the storage device.

When the scanned image signal is a non-standard image, the processing device generates a non-standard image notification signal.

The positioning assistance notifying device is electrically connected to the processing device.

When the positioning assistance notifying device receives the standard image notification signal generated by the processing device, the position assistance notifying device generates a standard image notification.

When the positioning assistance notifying device receives the non-standard image notification signal generated by the processing device, the position assistance notifying device generates a non-standard image notification.

The image scanning positioning assistance system can determine whether the image scanning device is operated accurately to check the scanning area of the human body according to the first classification probability values of the image types corresponding to the scanned image signal. When the image scanning device is operated accurately to finish checking the scanning area, the scanned image signal is stored into the storage device. The image scanning positioning assistance system can notify the operators according to the standard or non-standard image notification generated by the position assistance notifying device, such that the operators can determine whether the image scanning device is operated accurately. Therefore, even when the image scanning device is operated by personnel unfamiliar with it, the personnel can also determine whether the image scanning device is operated accurately according to the standard or non-standard image notification, thereby avoiding inaccurate inspection.

DETAILED DESCRIPTION OF THE INVENTION

Figure 1:
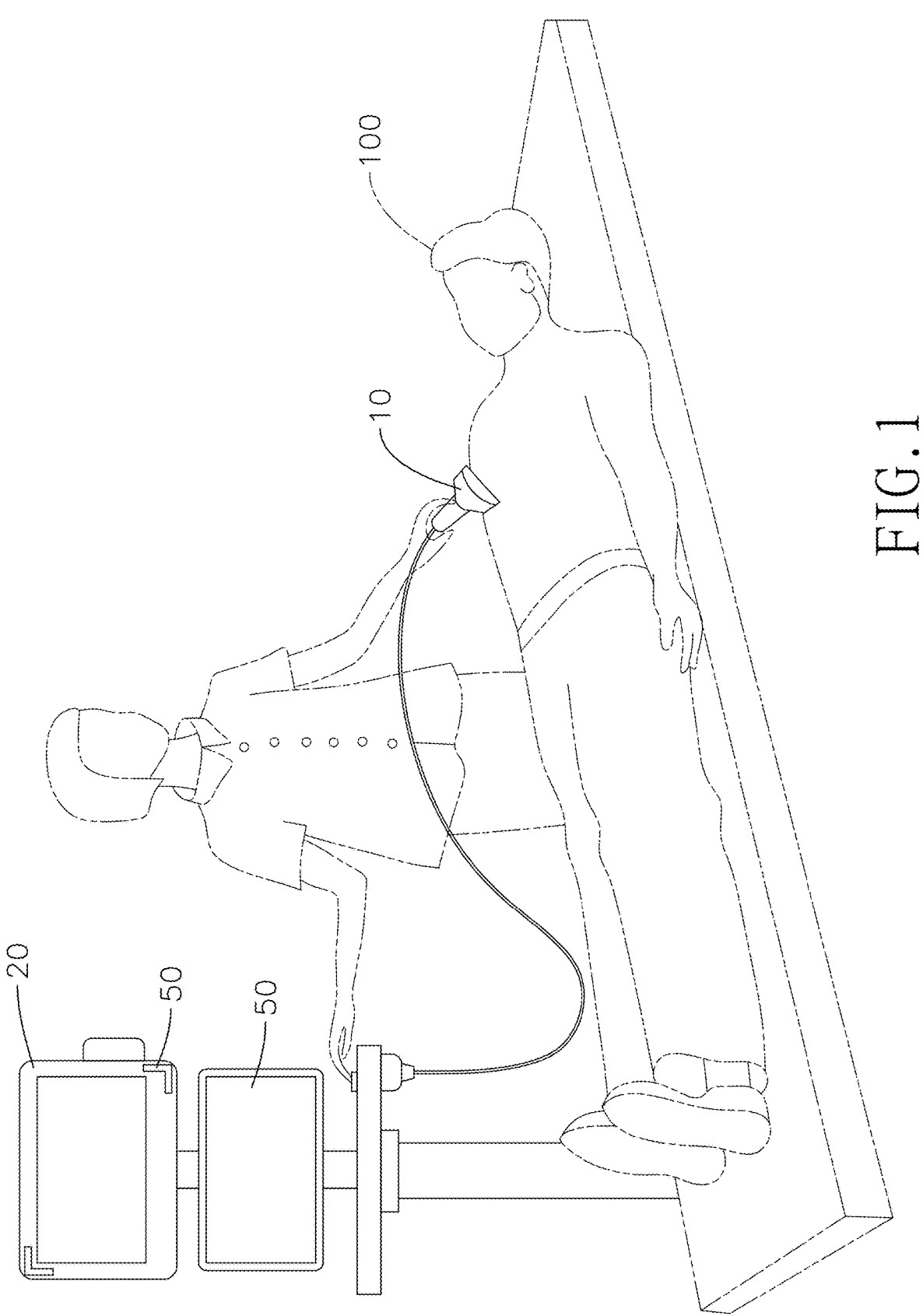
FIG. 1 is a schematic diagram of using an image scanning positioning assistance system of the present invention.
Figure 2:
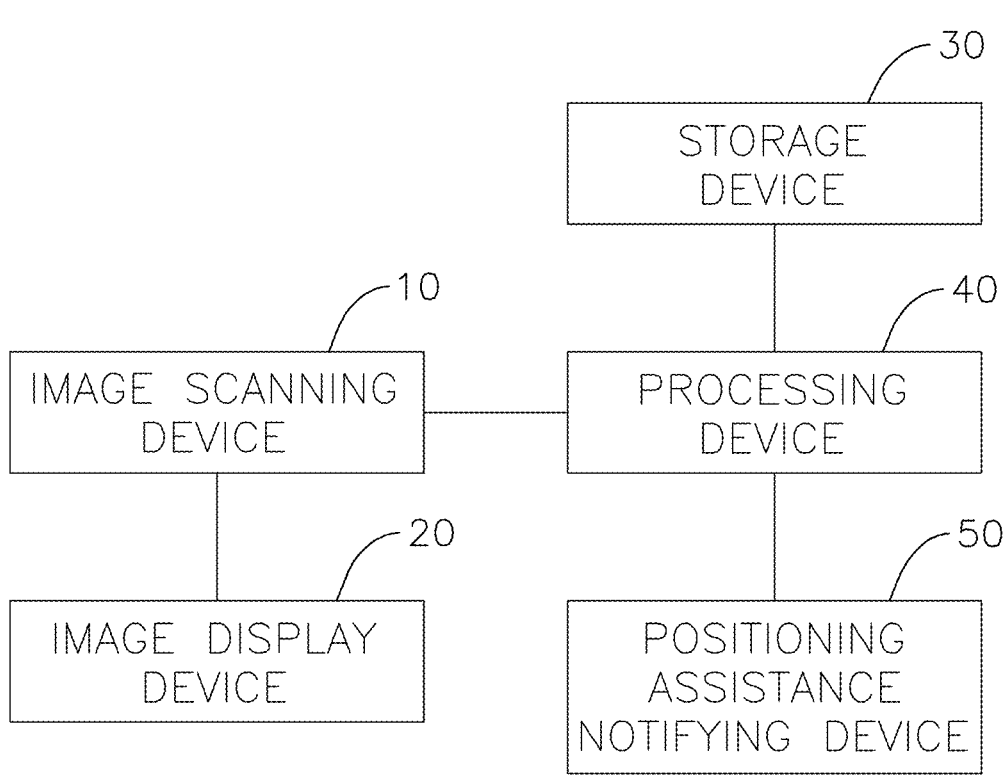
FIG. 2 is a block diagram of the image scanning positioning assistance system of the present invention.

With reference to FIGS. 1 and 2, the present invention is an image scanning positioning assistance system. The image scanning positioning assistance system includes an image scanning device 10, an image display device 20, a storage device 30, a processing device 40, and a positioning assistance notifying device 50.

The image scanning device 10 is used to scan a scanning area of a human body 100, and generates a scanned image signal. The image display device 20 is electrically connected to the image scanning device 10, receives the scanned image signal, and displays a scanned image according to the scanned image signal.

The storage device 30 stores a plurality of image types. The processing device 40 is communicatively connected to the image scanning device 10 and the storage device 30, receives the scanned image signal generated by the image scanning device 10, and respectively calculates a plurality of first classification probability values of the multiple image types corresponding to the scanned image signal. The processing device 40 further determines whether the scanned image signal is a standard image according to the first classification probability values. For example, in one embodiment, the storage device 30 is electrically connected to the processing device 40 for communication, and the storage device 30 and the processing device 40 are mounted together in a case. In another embodiment, the storage device 30 may be a cloud database, and the processing device 40 is communicatively connected to the storage device 30 via the Internet.

When the scanned image signal is the standard image, the processing device 40 generates a standard image notification signal, and stores the scanned image signal into the storage device 30. The image type corresponding to the standard image notification signal is the image type that has a maximum of the first classification probability values. When the scanned image signal is a non-standard image, the processing device 40 generates a non-standard image notification signal.

The positioning assistance notifying device 50 is electrically connected to the processing device 40. When the positioning assistance notifying device 50 receives the standard image notification signal generated by the processing device 40, the position assistance notifying device 50 generates a standard image notification. When the positioning assistance notifying device 50 receives the non-standard image notification signal generated by the processing device 40, the position assistance notifying device 50 generates a non-standard image notification.

The image scanning positioning assistance system can determine whether the image scanning device is operated accurately to check the scanning area of the human body 100 according to the first classification probability values of the image types corresponding to the scanned image signal. When the image scanning device is operated accurately to finish checking the scanning area, the processing device 40 stores the scanned image signal into the storage device 30. The image scanning positioning assistance system can notify the operators according to the standard or non-standard image notification generated by the position assistance notifying device 50, such that the operators can determine whether the image scanning device is operated accurately. Therefore, even when the image scanning device is operated by personnel unfamiliar with it, the personnel can also determine whether the image scanning device is operated accurately according to the standard or non-standard image notification, thereby avoiding inaccurate inspection.

In the embodiment, the processing device 40 can include an artificial intelligence (AI) model, such as a neural network module. The processing device 40 can be trained by machine learning methods according to a plurality of standard images with labels, such that the processing device 40 can generate the first classification probability values of the image types corresponding to the scanned image signal. The machine learning methods may average weighted characteristic values, such as the logistic regression, the support vector machine (SVM), the artificial neural network, etc.

In the embodiment, the positioning assistance notifying device 50 can generate the standard or non-standard image notification by lighting, voicing, or displaying images or characters. With reference to FIG. 1, the positioning assistance notifying device 50 can be an L-shaped light-emitting diode (LED) mounted on a frame of the image display device 20, and generates the standard or non-standard image notification by lighting the L-shaped LED. For example, the standard image notification may be a green light, and the non-standard image notification may be a red light. Therefore, the operator can determine whether the scanning area has been checked according to the positioning assistance notifying device 50. In another embodiment, the positioning assistance notifying device 50 may be a speaker or a monitor.

Moreover, in the embodiment, the image scanning device 10 can be a scanning device which can display a scanned result by image, such as an ultrasound machine or an ophthalmoscope.

Figure 3:
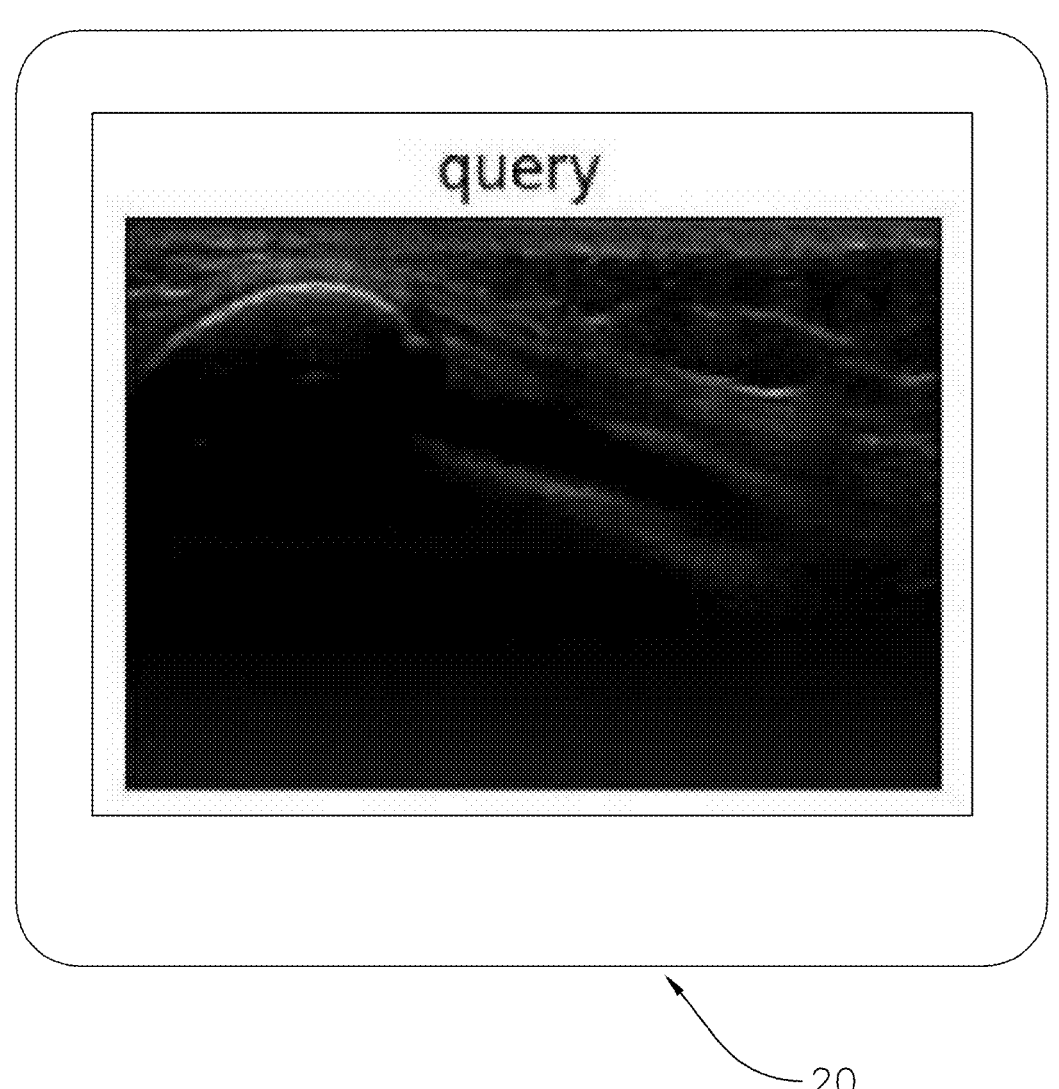
FIG. 3 is a schematic diagram of a scanned image of the image scanning positioning assistance system of the present invention.

With reference to FIG. 3, in this embodiment, the image scanning device 10 may be the ultrasound machine, and the ultrasound machine is used to scan a knee of the human body. Then, the image display device 20 can display the scanned image, such as an ultrasound image of the knee of the human body.

In one embodiment, when determining whether the scanned image signal is the standard image according to the first classification probability values, the processing device 40 determines whether the image type with the maximum of the first classification probability values of the image types corresponding to the scanned image signal is a non-standard image type. When the image type with the maximum of the first classification probability values of the image types corresponding to the scanned image signal is not the non-standard image type, the processing device 40 determines that the scanned image signal is the standard image. When the image type with the maximum of the first classification probability values of the image types corresponding to the scanned image signal is the non-standard image type, the processing device 40 determines that the scanned image signal is not the standard image.

In another embodiment, when determining whether the scanned image signal is the standard image according to the first classification probability values, the processing device 40 determines whether the maximum of the first classification probability values of the image types corresponding to the scanned image is greater than a threshold value. When the maximum of the first classification probability values of the image types corresponding to the scanned image signal is greater than the threshold value, the processing device 40 determines the scanned image signal is the standard image. When the maximum of the first classification probability values of the image types corresponding to the scanned image signal is not greater than the threshold value, the processing device 40 determines the scanned image signal is not the standard image.

Moreover, the storage device 30 further stores a plurality of standard image signals and a plurality of standard image types. The standard images each correspond to a respective one of the standard image types. When the processing device 40 generates the non-standard image notification, the processing device 40 further determines a most similar standard image type according to the scanned image signal and the standard image signals, and the processing device 40 generates a positioning assistance notification according to the most similar standard image type.

In the embodiment, the standard image types are scanned images of standard positions in the scanning area. For example, when the image scanning device 10 is used to ultrasonically scan the knee of the human body, the standard positions of the knee of the human body include seven positions, and therefore the standard image types includes seven types. Since the scanned images of the same standard position of different human bodies may differ, the standard image types each may correspond to multiple standard image signals, and the standard image signals corresponding to the same standard image type may be similar, but not necessarily identical.

When a scanning procedure is performed, sometimes the operator needs to scan the seven standard positions for generating at least seven scanned image signals corresponding to the seven standard image types. Therefore, the operaand the image notification is displayed by a monitor. For example, the unscanned standard image type notification is a schematic diagram of a knee, marked with a plurality of standard positions. In the schematic diagram of the knee, a scanned standard position is marked by a filled circle, and an unscanned standard position is marked by a hollow circle. Therefore, the operator can determine whether there is an unscanned standard image signal according to the unscanned standard image type notification, and the unscanned standard image type notification can further notify the operator of a position corresponding to the unscanned standard image signal, such that the operator can accurately and efficiently finish the scanning procedure.

In the embodiment, when the processing device 40 determines the most similar standard image type according to the scanned image signal and the standard image signals, the processing device 40 determines that the image type corresponding to a second largest value of the first classification probability values is the most similar standard image type. For example, as shown in table 1, the image type corresponding to the maximum of the first classification probability values is the "non-standard image type", and the image type corresponding to the second largest value of the first classification probability values is the "lat_med". Since the image type corresponding to the maximum of the first classification probability values is the non-standard image type, the processing device 40 generates the non-standard image notification signal. Otherwise, the processing device 40 generates the standard image notification signal.

TABLE 1

| | Image Type | | | | | | | |
| | lat_med | infra_p | LFTJ | post | MFTJ | supra_p | Trans | non-standard image type |
| --- | --- | --- | --- | --- | --- | --- | --- | --- |
| First Classification Probability Value | 20% | 8% | 3% | 2% | 0% | 0% | 0% | 67% | tor operates the image scanning device 10 to sequentially scan the seven standard positions of the knee of the human body. However, scanning the standard position does not mean that the scanned image signal always corresponds to the standard image signal. Therefore, the positioning assistance notifying device 50 can be used to notify the operator whether the scanned image signal corresponds to the standard image signal, such that accuracy and efficiency of the scanning procedure can be improved.

Moreover, when the processing device 40 stores the scanned image signal to the storage device 30, the processing device 40 further determines that the image type corresponding to the standard image notification signal is a scanned standard image type. The processing device 40 generates an unscanned standard image type notification signal according to the standard image type not corresponding to the scanned standard image type. When the positioning assistance notifying device 50 receives the unscanned standard image type notification signal generated by the processing device 40, the positioning assistance notifying device 50 generates an unscanned standard image type notification.

Figure 4:
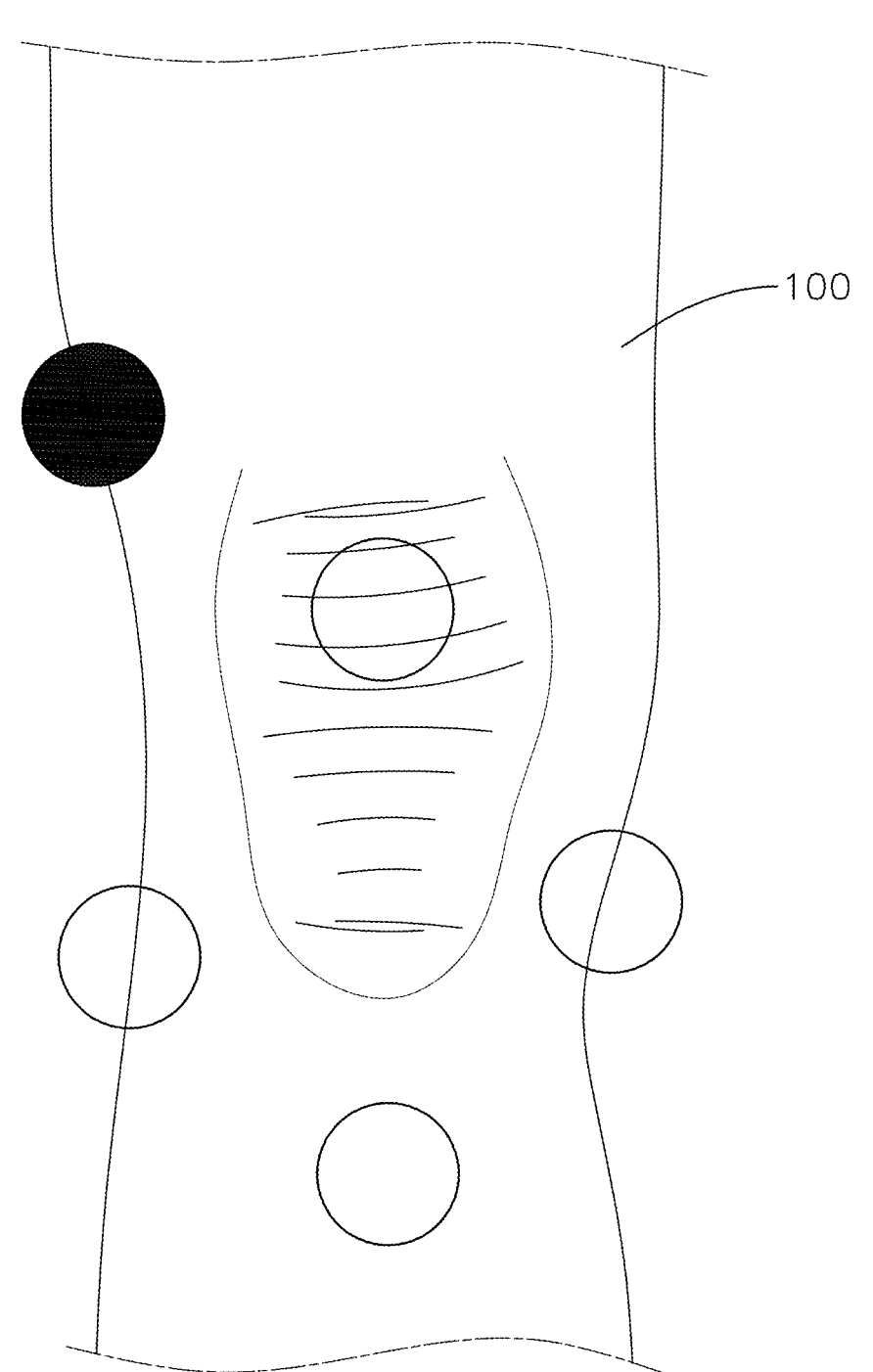
FIG. 4 is a schematic diagram of an unscanned standard image type notification of the image scanning positioning assistance system of the present invention.
Figure 5A:
FIGS. 5A-5J are schematic diagrams of similar standard images of the image scanning positioning assistance system of the present invention.

Furthermore, with reference to FIG. 4, the unscanned standard image type notification generated by the positioning assistance notifying device 50 is an image notification, Further, in another embodiment, when the processing device 40 determines the most similar standard image type according to the scanned image signal and the standard image signals, the processing device 40 calculates image similarities of the scanned image signal and the standard image signals. Namely, the scanned image signal and each of the standard image signals may correspond to one image similarity. The processing device 40 further determines that the standard image type corresponding to the standard image signal having a maximum of the image similarities is the most similar standard image type. For example, with reference to FIGS. 4 and 5A, the processing device 40 determines that the scanned image signal shown in FIG. 4 is the most similar with the standard image signal shown in FIG. 5A. Namely, the standard image signal shown in FIG. 5A has the maximum of the image similarities. The image similarity of the standard image signal shown in FIG. 5A is 0.32, and the standard image type corresponding to the standard image signal shown in FIG. 5A is "lat_med". Therefore, the processing device 40 determines that the most similar standard image type corresponding to the scanned image signal shown in FIG. 4 is "lat_med".

The scanned image signal and the standard image signals each can be an original image, and whether the scanned image signal is similar with the standard image signals can be determined by matching the original images. Moreover, the scanned image signal and the standard image signal each can be an image feature vector, and whether the scanned image signal is similar with the standard image signals can be determined by matching the image feature vectors. It is not necessary to match the original images.

In another embodiment, when the processing device 40 determines the most similar standard image type according to the scanned image signal and the standard image signals, the processing device 40 calculates image similarities of the scanned image signal and the standard image signals. Namely, the scanned image signal and each of the standard image signals may correspond to one image similarity. The processing device 40 further determines a plurality of similar standard image signals which are similar with the scanned image signal from the standard image signals.

The processing device 40 further determines the image type corresponding to the second largest value of the first classification probability values, determines the standard image type corresponding to the similar standard image signal having the maximum of the image similarities, and determines the standard image type corresponding to the similar standard image signals having the largest number. Then, the processing device 40 calculates second classification probability values of the multiple image types corresponding to the scanned image according to the image type corresponding to the second largest value of the first classification probability values, the standard image type corresponding to the similar standard image signal having the maximum of the image similarities, and the standard image type corresponding to the similar standard image signals having the largest number. Moreover, the processing device 40 determines that the most similar standard image type is the standard image type having a maximum of the second classification probability values.

Figure 5B:
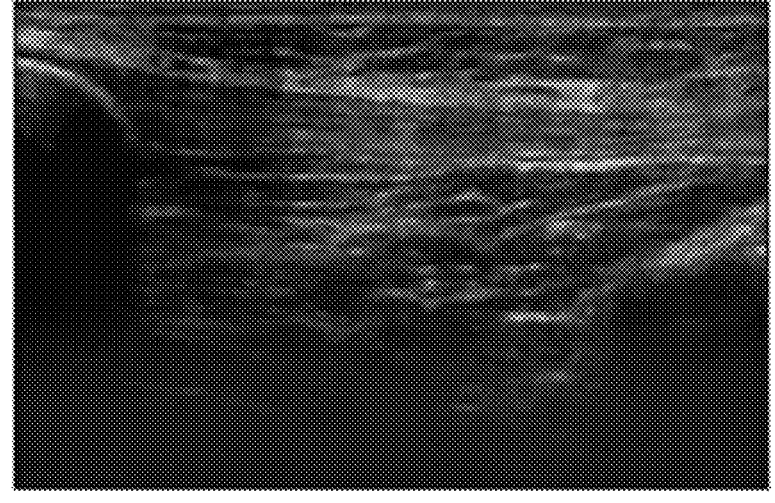
Figure 5C:
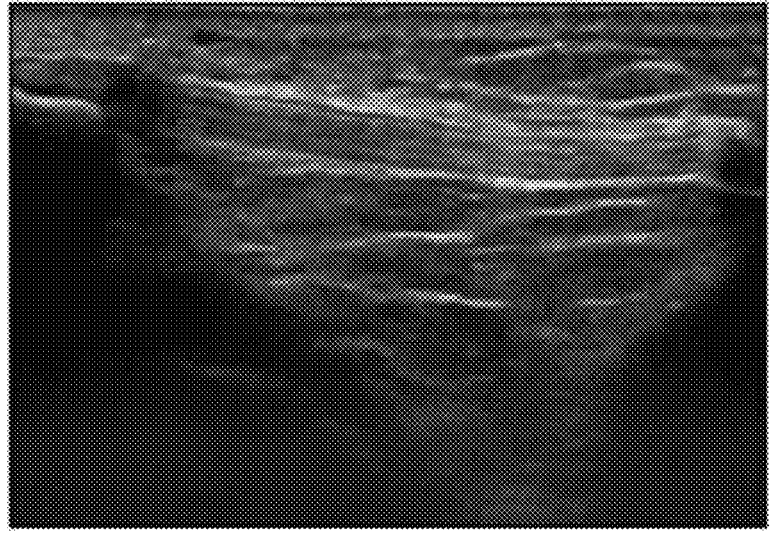
Figure 5D:
Figure 5E:
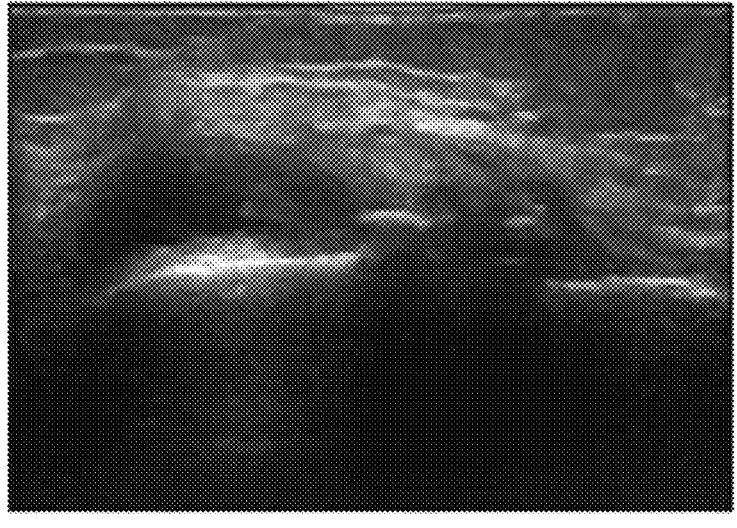
Figure 5F:
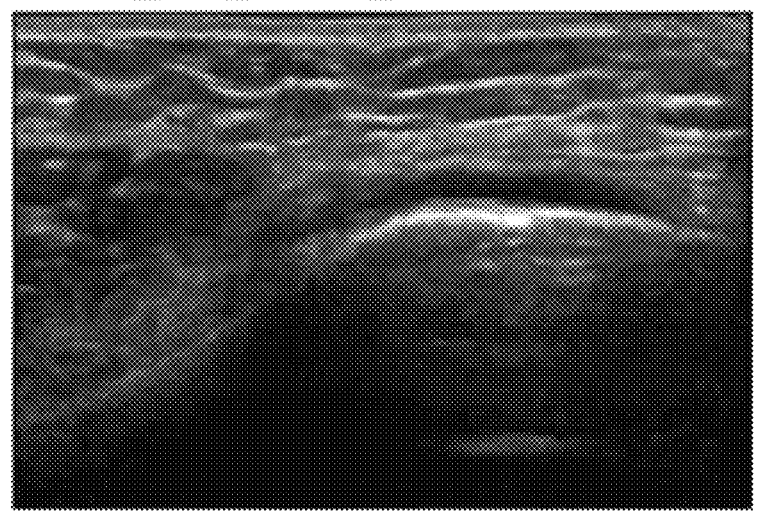
Figure 5G:
Figure 5H:
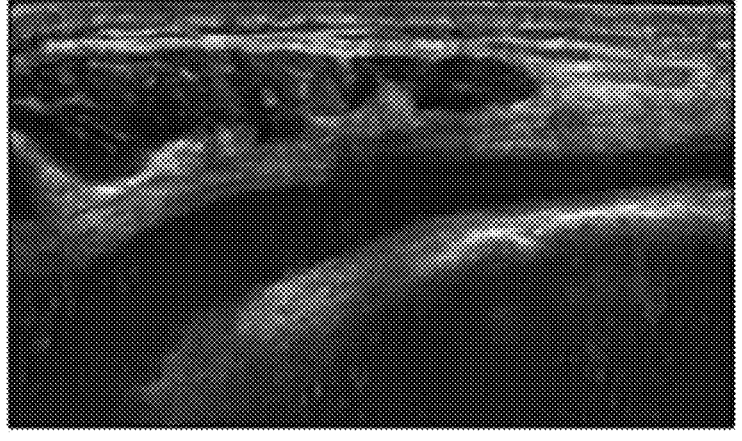
Figure 5I:
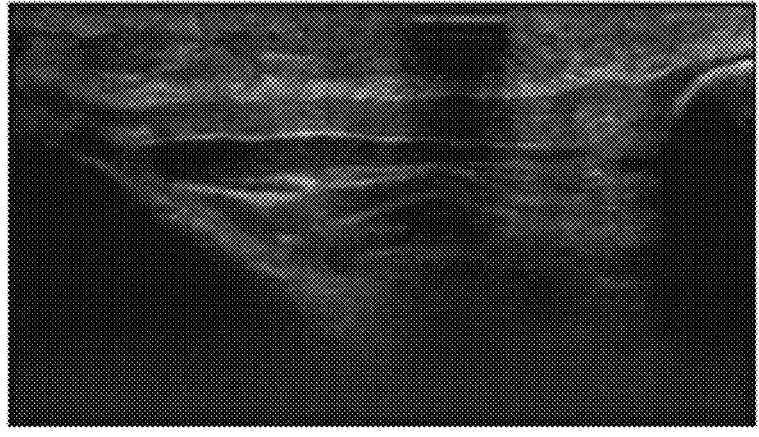
Figure 5J:

For example, with reference to FIGS. 5A to 5J, the processing device 40 determines the ten standard image signals as shown in FIG. 5A to 5J similar with the scanned image signal as shown in FIG. 3 from all of the standard in FIG. 5F is 0.29, and the standard image type corresponding to the standard image signal as shown in FIG. 5F is "lat_med". The image similarity of the standard image signal as shown in FIG. 5G is 0.27, and the standard image type corresponding to the standard image signal as shown in FIG. 5G is "post". The image similarity of the standard image signal as shown in FIG. 5H is 0.27, and the standard image type corresponding to the standard image signal as shown in FIG. 5H is "lat_med". The image similarity of the standard image signal as shown in FIG. 5I is 0.27, and the standard image type corresponding to the standard image signal as shown in FIG. 5I is "infra_p". The image similarity of the standard image signal as shown in FIG. 5J is 0.26, and the standard image type corresponding to the standard image signal as shown in FIG. 5J is "infra_p".

In the embodiment, according to the table 1, the standard image type corresponding to the maximum of the first classification probability values is "lat_med". The processing device 40 determines that the similar standard image signal having the maximum of the image similarities is the standard image signal as shown in FIG. 5A, and the standard image type corresponding to the similar standard image signal having the maximum of the image similarities is "lat_med". The processing device 40 determines the similar standard image signals having the largest number are the standard image signals as shown in FIGS. 5B, 5C, 5D, 5I, and 5J, and the standard image type corresponding to the similar standard image signals having the largest number is "infra_p".

Moreover, the processing device 40 calculates the second classification probability values of the multiple image types corresponding to the scanned image according to the image type corresponding to the second largest value of the first classification probability values, the standard image type corresponding to the similar standard image signal having the maximum of the image similarities, and the standard image type corresponding to the similar standard image signals having the largest number. For example, the second classification probability values are shown in table 2.

TABLE 2

| | Standard Image Type | | | | | | |
|---|---|---|---|---|---|---|---|
| | lat_med | infra_p | LFTJ | post | MFTJ | supra_p | trans |
| Second Classification Probability Values | 41% | 52% | 5% | 2% | 0% | 0% | 0% | image signals. The image similarity of the standard image signal as shown in FIG. 5A is 0.32, and the standard image type corresponding to the standard image signal as shown in FIG. 5A is "lat_mad". The image similarity of the standard image signal as shown in FIG. 5B is 0.32, and the standard image type corresponding to the standard image signal as shown in FIG. 5B is "infra_p". The image similarity of the standard image signal as shown in FIG. 5C is 0.30, and the standard image type corresponding to the standard image signal as shown in FIG. 5C is "infra_p". The image similarity of the standard image signal as shown in FIG. 5D is 0.30, and the standard image type corresponding to the standard image signal as shown in FIG. 5D is "infra_p". The image similarity of the standard image signal as shown in FIG. 5E is 0.30, and the standard image type corresponding to the standard image signal as shown in FIG. 5E is "LFTJ". The image similarity of the standard image signal as shown Accordingly, the processing device 40 determines that the most similar standard image type is the standard image type having a maximum of the second classification probability values. Namely, the processing device 40 determines that the most similar standard image type is "infra_p".

In this embodiment, the processing device 40 includes an AI model. The AI model is trained by a vast quantity of the standard image signals, such that the AI model can determine whether the scanned image signal is similar with the standard image signals. When the scanned image signal is not similar with any one of the standard image signals, the AI model can further infer the standard image signal which is the most similar with the scanned image signal, and the AI model can notify the operator according to the inferred standard image signal.

For example, the AI model can notify the operator by voicing, or displaying images or characters. Each of the standard image types corresponds to a respective one of the standard positions, provided with tutorials for scanning at each of the standard positions, such that a beginner or a learner can learn how to scan the standard positions. Therefore, when the AI model infers the standard image signal which is the most similar with the scanned image signal, the AI model can notify the operator according to the most similar standard image type corresponding to the inferred standard image signal through the positioning assistance notifying device 50. The positioning assistance notifying device 50 can notify the operator by voicing, or displaying the teaching materials or the teaching methods, and the operator can scan the standard positions according to notification generated by the positioning assistance notifying device 50. The operator can further correspondingly adjust scanning positions according to the notification generated by the positioning assistance notifying device 50. Therefore, the operator can accurately and efficiently finish the scanning procedure.

Moreover, in another embodiment, when the processing device 40 determines the ten standard image signals as shown in FIGS. 5A to 5J similar with the scanned image signal as shown in FIG. 3 from all of the standard image signals, the processing device 40 can calculate the second classification probability values of the multiple image types corresponding to the scanned image according to the image type corresponding to the second largest value of the first classification probability values, such as "lat_med", the types and the numbers of the standard image type corresponding to the similar standard image signals having the largest number, such as three "lat_med", five "infra_p", one "LFTJ", and one "post", which are shown in FIGS. 5A to 5J.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:

1. An image scanning positioning assistance system, comprising:
an image scanning device, scanning a scanning area of a human body, and generating a scanned image signal;
an image display device, electrically connected to the image scanning device, receiving the scanned image signal, and displaying a scanned image according to the scanned image signal;
a storage device, storing a plurality of image types;
a processing device, communicatively connected to the image scanning device and the storage device, receiving the scanned image signal generated by the image scanning device, and respectively calculating a plurality of first classification probability values of the multiple image types corresponding to the scanned image signal;
wherein the processing device further determines whether the scanned image signal is a standard image according to the first classification probability values;
wherein when the scanned image signal is the standard image, the processing device generates a standard image notification signal, and stores the scanned image signal into the storage device;

wherein when the scanned image signal is a non-standard image, the processing device generates a non-standard image notification signal;
a positioning assistance notifying device, electrically connected to the processing device;
wherein when the positioning assistance notifying device receives the standard image notification signal generated by the processing device, the position assistance notifying device generates a standard image notification;
wherein when the positioning assistance notifying device receives the non-standard image notification signal generated by the processing device, the position assistance notifying device generates a non-standard image notification.

2. The image scanning positioning assistance system as claimed in claim 1, wherein when the processing device determines whether the scanned image signal is the standard image according to the first classification probability values, the processing device determines whether the image type with the maximum of the first classification probability values of the image types corresponding to the scanned image signal is a non-standard image type;
wherein when the image type with the maximum of the first classification probability values of the image types corresponding to the scanned image signal is not the non-standard image type, the processing device determines that the scanned image signal is the standard image;
wherein when the image type with the maximum of the first classification probability values of the image types corresponding to the scanned image signal is the non-standard image type, the processing device determines that the scanned image signal is not the standard image.

3. The image scanning positioning assistance system as claimed in claim 2, wherein the storage device further stores a plurality of standard image signals and a plurality of standard image types, and the standard image signals each correspond to a respective one of the standard image types;
wherein when the processing device generates the non-standard image notification, the processing device further determines a most similar standard image type according to the scanned image signal and the standard image signals, and the processing device generates a positioning assistance notification according to the most similar standard image type.

4. The image scanning positioning assistance system as claimed in claim 3, wherein when the processing device determines the most similar standard image type according to the scanned image signal and the standard image signals, the processing device determines that the image type corresponding to a second largest value of the first classification probability values is the most similar standard image type.

5. The image scanning positioning assistance system as claimed in claim 3, wherein when the processing device determines the most similar standard image type according to the scanned image signal and the standard image signals, the processing device calculates image similarities of the scanned image signal and the standard image signals, and the processing device determines that the standard image type corresponding to the standard image signal having a maximum of the image similarities is the most similar standard image type.

6. The image scanning positioning assistance system as claimed in claim 3, wherein when the processing device determines the most similar standard image type according to the scanned image signal and the standard image signals, the processing device calculates image similarities of the scanned image signal and the standard image signals, and the processing device determines a plurality of similar standard image signals which are similar with the scanned image signal from the standard image signals;

wherein the processing device further determines the image type corresponding to a second largest value of the first classification probability values, determines the standard image type corresponding to the similar standard image signal having the maximum of the image similarities, and determines the standard image type corresponding to the similar standard image signals having the largest number;

wherein the processing device further calculates second classification probability values of the multiple image types corresponding to the scanned image according to the image type corresponding to the second largest value of the first classification probability values, the standard image type corresponding to the similar standard image signal having the maximum of the image similarities, and the standard image type corresponding to the similar standard image signals having the largest number;

wherein the processing device determines that the most similar standard image type is the standard image type having a maximum of the second classification probability values.

7. The image scanning positioning assistance system as claimed in claim 2, wherein the image type corresponding to the standard image notification signal is the image type having a maximum of the first classification probability values.

8. The image scanning positioning assistance system as claimed in claim 7, wherein the storage device further stores a plurality of standard image types;

wherein when the processing device stores the scanned image signal to the storage device, the processing device further determines that the image type corresponding to the standard image notification signal is a scanned standard image type, and the processing device generates an unscanned standard image type notification signal according to the standard image type not corresponding to the scanned standard image type;

wherein when the positioning assistance notifying device receives the unscanned standard image type notification signal generated by the processing device, the positioning assistance notifying device generates an unscanned standard image type notification.

9. The image scanning positioning assistance system as claimed in claim 1, wherein the positioning assistance notifying device generates the standard image notification or the non-standard image notification by lighting, voicing, or displaying images or characters;

wherein the image scanning device is an ultrasound machine or an ophthalmoscope.

10. The image scanning positioning assistance system as claimed in claim 1, wherein when the processing device determines whether the scanned image signal is the standard image according to the first classification probability values, the processing device determines whether the maximum of the first classification probability values of the image types corresponding to the scanned image signal is greater than a threshold value;

wherein when the maximum of the first classification probability values of the image types corresponding to the scanned image signal is greater than the threshold value, the processing device determines the scanned image signal is the standard image;

wherein when the maximum of the first classification probability values of the image types corresponding to the scanned image signal is not greater than the threshold value, the processing device determines the scanned image signal is not the standard image.

* * * * *